United States Patent
Liu et al.

(10) Patent No.: US 8,076,499 B2
(45) Date of Patent: Dec. 13, 2011

(54) METHOD FOR PREPARING PRECURSOR OF RADIOACTIVE 3-IODOBENZYLGUANIDINE

(75) Inventors: Show-Wen Liu, Shetou Township, Changhua County (TW); Cheng-Hsien Lin, Taipei (TW); Tsyh-Lang Lin, Bade (TW); Cheng-Fang Hsu, Toufen Township, Miaoli County (TW)

(73) Assignee: Atomic Energy Council-Institute of Nuclear Energy Research, Taoyuan County (TW)

( * ) Notice: Subject to any disclaimer, the term of this patent is extended or adjusted under 35 U.S.C. 154(b) by 117 days.

(21) Appl. No.: 12/540,448

(22) Filed: Aug. 13, 2009

(65) Prior Publication Data

US 2011/0040119 A1 Feb. 17, 2011

(51) Int. Cl.
*C07F 3/10* (2006.01)
*C07F 7/00* (2006.01)
(52) U.S. Cl. .......................................... 556/36; 556/107
(58) Field of Classification Search .................. None
See application file for complete search history.

(56) References Cited

OTHER PUBLICATIONS

Vaidynathan et al, Journal of Labeled compounds and Radiopharmaceuticals, A Tin Precursor for the Synthesis of No-carrier-added [*I]MIBG and [211At]MABG, 2007, 50, pp. 177-182.*

* cited by examiner

*Primary Examiner* — Paul A Zucker
(74) *Attorney, Agent, or Firm* — Ming Chow; Sinorica, LLC

(57) ABSTRACT

A method for preparing a precursor of radioactive 3-iodobenzylguanidine- N,N'-bis(tert-butyloxycarbonyl)-3-(tri-n-butyltin)benzylguanidine) (MSnBG) is revealed. The method includes following steps. Firstly, obtain 3-iodobenzylguanidine bicarbonate by an addition reaction between 3-iodobenzylamine hydrochloride and cyanamide. Use di-tert-butyl dicarbonate as a protecting agent for NH group and convert 3-iodobenzylguanidine bicarbonate into N,N'-bis(tert-butyloxycarbonyl)-N-(3-iodobenzyl) guanidine. At last, under catalysis of bis(triphenylphosphine) palladium dichloride, obtain a final product MSnBG by a substitution reaction between N,N'-bis(tert-butyloxycarbonyl)-N-(3-iodobenzyl) guanidine and bis(tri-n-butyltin). MSnBG is used in no-carrier-added synthesis of [*I]MIBG.

7 Claims, 3 Drawing Sheets

METHOD FOR PREPARING PRECURSOR OF RADIOACTIVE 3-IODOBENZYLGUANIDINE

BACKGROUND OF THE INVENTION

1. Field of Invention

The present invention relates to a method for preparing a precursor of radioactive agents, especially to a method for preparing N,N'-bis(tert-butyloxycarbonyl)-3-(tri-n-butyltin)benzylguanidine) (MSnBG), a precursor of radioactive 3-iodobenzylguanidine.

2. Description of Related Art

After being found in 1980s, 3-iodobenzylguanidine (Meta-iodo-benzyl-guanidine, MIBG) labeled with I-123 and I-131 ([$^{123}$I]MIBG and [$^{131}$I]MIBG) has been used as imaging agents for diagnosis of various diseases such as heart diseases and neuroblastoma. Moreover, the half-life of I-131 gives the value 80.5 days and the energy released per decay is 0.97 MeV so that it can be used for the radiation therapy of tumors. Thus [$^{131}$I]MIBG is also used as an antineoplastic agent for treatment of neuroblastoma in the image-guided radiation therapy.

For a long time, radioiodine labeled MIBG([*I]MIBG) is prepared by an isotopic exchange method using an radioiodide (I-131 or I-125), as shown in FIG. 1. Beside MIBG with radioactive iodine, the product obtained by this method contains a significant amount of initial reactant-MIBG with natural iodine. The two materials are difficult to separate with each other. While being applied to antineoplastic agents, after being injected into humans, [*I]MIBG and MIBG compete with each other to bind with specific receptors. The amount of MIBG is far more larger than the [*I]MIBG so that a large amount of receptors are occupied by MIBG. Thus effective [*I]MIBG is unable to react with receptors and the effects of radiation therapy have been affected.

Although in the study of G. Vaidyanathan, D. J. Affleck, K. L. Alaton and M. R. Zalutsky, J. Label. Comp. Radiopharm., 50, 177-182 (2007), a similar precursor to be labeled is revealed. However, a method for manufacturing the precursor is disclosed by Dodd and A. P. Kozikowski, Tetrahedron Lett., 35, 977-979 (1994) and G. Vaidyanathan and M. R. Zalutsky, J. Org. Chem., 62, 4867-4869 (1997), as shown in FIG. 2. Moreover, the leaving group of the precursor (C14) to be labeled is (CH$_3$)$_3$Sn.

SUMMARY OF THE INVENTION

Therefore it is a primary object of the present invention to provide a method for preparing a precursor for radioactive agents-N,N'-bis(tert-butyloxycarbonyl)-3-(tri-n-butyltin)benzylguanidine) (MSnBG). The Bu$_3$Sn is an optimal leaving group that is easy to be replaced in a substitution reaction.

It is another object of the present invention to provide a method for preparing a precursor for radioactive drugs-N,N'-bis(tert-butyloxycarbonyl)-3-(tri-n-butyltin)benzylguanidine) (MSnBG) that includes simple reaction steps. After completion of the reaction, the product is obtained only after filtering and washing. There are no complicated separation and purification processes.

In order to achieve objects, a method for preparing a precursor for radioactive drugs-N,N'-bis(tert-butyloxycarbonyl)-3-(tri-n-butyltin)benzylguanidine) (MSnBG) according to the present invention includes a plurality of simple reaction steps. After the reactions, the compound is obtained after filtering and washing, without complicated separation and purification procedures. The Bu$_3$Sn of MSnBG is an optimal leaving group that is easy to be replaced by another group in a substitution reaction. Moreover, the MSnBG is to prepare no-carrier-added radioactive [*I]MIBG that is used as radioactive imaging agents and antineoplastic drugs. The [*I] MIBG obtained by this method has better effect on neuroblastoma treatment than that obtained by conventional, carrier-added method.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

In conventional techniques, the leaving group in the labeled precursor (C14) is (CH$_3$)$_3$Sn. In a substitution reaction, the loss of the (CH$_3$)$_3$Sn is not as easy as Bu$_3$Sn of the present invention. This is due to that the more carbons the compound has, the lower the polarity it has.

The compound becomes more soluble in solvents. The later group (Bu3Sn) is better than the former group (CH3)3Sn due to better solvation effect and easy leaving during reaction. Moreover, besides MIBG with radioactive iodine, the MIBG prepared by conventional techniques contains large amount of initial reactant-MIBG with natural iodine. Yet the product prepared by the present method contains no natural iodine.

Figure 1:
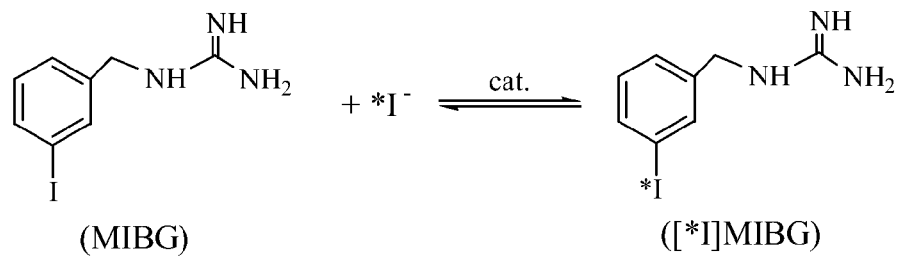
FIG. 1 is a reaction equation of [*I]MIBG in a conventional technique.
Figure 2:
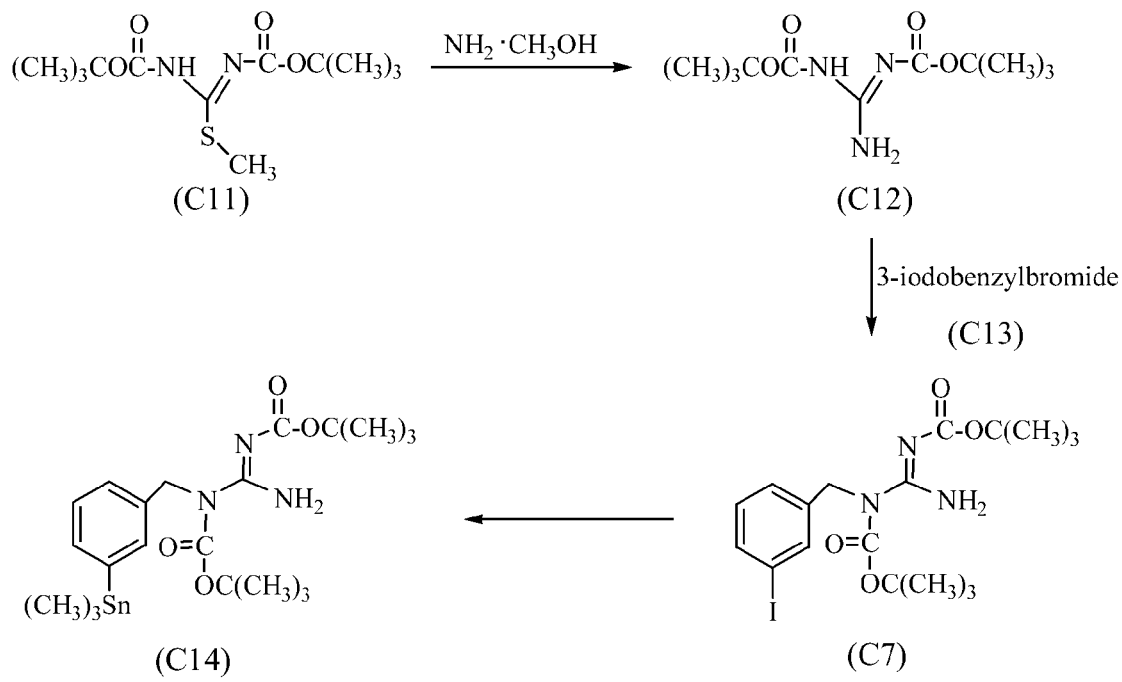
FIG. 2 shows reaction equations of another precursor-compound C14 in a conventional technique.
Figure 3A:
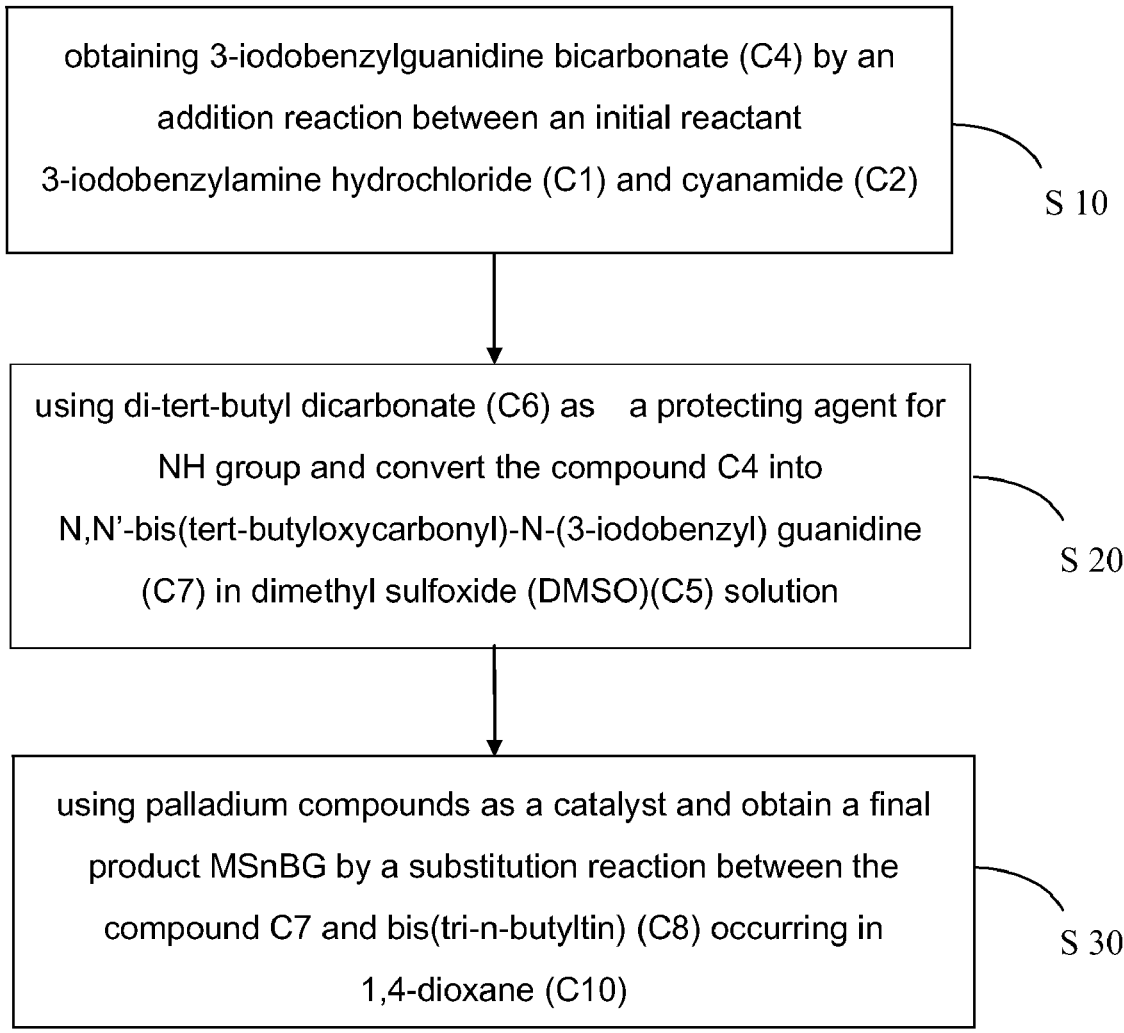
FIG. 3A is a flow chart showing manufacturing processes of an embodiment of MSnBG according to the present invention.
Figure 3B:
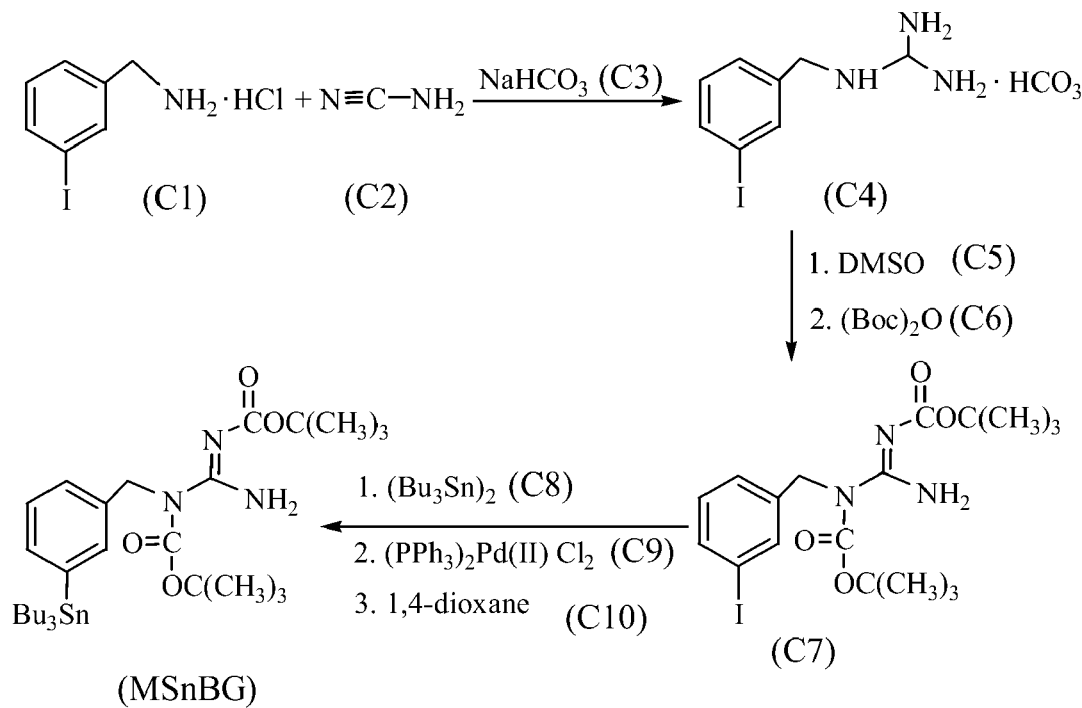
FIG. 3B shows reaction equations of an embodiment of MSnBG according to the present invention.

Refer to FIG. 3A and FIG. 3B, a method for preparing N,N'-bis(tert-butyloxycarbonyl)-3-(tri-n-butyltin)benzylguanidine (MSnBG) includes the following steps:

Step S10: obtaining 3-iodobenzylguanidine bicarbonate (C4) by an addition reaction between an initial reactant 3-iodobenzylamine hydrochloride (C1) and cyanamide (C2);

Step S20: using di-tert-butyl dicarbonate (C6) as a protecting agent for NH group and convert the compound C4 into N,N'-bis(tert-butyloxycarbonyl)-N-(3-iodobenzyl) guanidine (C7) in dimethyl sulfoxide (DMSO)(C5) solution; and Step S30: using palladium compounds as a catalyst and obtain a final product MSnBG by a substitution reaction between the compound C7 and bis(tri-n-butyltin) (C8) occurring in 1,4-dioxane (C10).

In the step S10, the synthesis of 3-iodobenzylguanidine bicarbonate (C4) is as following: take 5.88 g (21.8 mmol) 3-iodobenzylamine hydrochloride (C1) and 2.06 g (47.96 mmol) cyanamide (C2) to form a mixture that is heated and refluxed at 105 degrees Celsius for 4 hours. After cooling down, add water (10 mL) into the mixture to dissolve completely. Then add 10 mL aqueous solution of sodium bicarbonate (C3) (1.83 g, 21.8 mmol) to obtain an insoluble solid (precipitate). After filtering, washing with cold water, acetone and ether and drying, the compound C4 (6.7 g, 91%) is obtained.

Analysis of the synthesis product: IR (KBr) ν 3352 (NH), 1697 (CO) cm$^{-1}$. $^1$H NMR (CD$_3$OD) δ 7.71 (s, 1 H, C$_6$H$_4$), 7.68 (d, J=7.8 Hz, 1 H, C$_6$H$_4$), 7.33 (d, J=7.8 Hz, 1 H, C$_6$H$_4$), 7.15 (t, J=7.8 Hz, 1 H, C$_6$H$_4$), 4.36 (s, 2 H, CH$_2$). $^{13}$C NMR (CD$_3$OD) δ 160.51 (CO), 157.67 (C=N), 139.27, 136.92, 136.12, 130.52, 126.41 and 94.0 (C$_6$H$_4$), 43.58 (CH$_2$)○

In the step S20, the synthesis of N,N'-bis(tert-butyloxycarbonyl)-N-(3-iodobenzyl) guanidine (C7) is as following: Dissolve the compound C4 (6.7 g, 19.9 mmol) in 30 mL anhydrous dimethyl sulfoxide (C5) and add di-tert-butyl dicarbonate (C6) (11.0 mL, 46.4 mmol). Stir the solution at room temperature overnight and a solid is precipitated. After filtering, washing with water and drying, a product C7 (7.3 g, 77%) is obtained.

Analysis of the synthesis product: IR (KBr) ν 3386 (NH), 1717 (CO) cm$^{-1}$. $^1$H NMR (CDCl$_3$) δ 9.2-9.5 (br, 2 H, NH$_2$), 7.64 (s, 1 H, C$_6$H$_4$), 7.57 (d, J=7.8 Hz, 1 H, C$_6$H$_4$), 7.24 (d, J=7.8 Hz, 1 H, C$_6$H$_4$), 7.03 (t, J=7.8 Hz, 1 H, C$_6$H$_4$), 5.11 (s, 2 H, CH$_2$), 1.50 (s, 9 H, Bu), 1.37 (s, 9 H, Bu). $^{13}$C NMR (CDCl$_3$) δ 163.58 and 160.55 (CO), 154.67 (C=N), 141.14, 136.52, 135.93, 129.91, 126.40 and 93.84 (C$_6$H$_4$), 84.35 and 78.93 (C(CH$_3$)$_3$), 46.78 (CH$_2$), 28.25 and 27.80 (CH$_3$). MS m/z 475 (M$^+$)○

In the step S30, the synthesis of N,N'-bis(tert-butyloxycarbonyl)-3-(tri-n-butyltin)benzylguanidine) (MSnBG) is as following: Dissolve the compound C7 (1.111 g, 2.34 mmol), 1.75 mL (3.51 mmol) bis(tri-n-butyltin) (C8) and bis(triphenylphosphine) palladium dichloride (C9) (0.16 g, 0.23 mmol) in 30 mL anhydrous 1,4-dioxane (C10) and heat the solution at 80 degrees Celsius for 5 hours. After filtering, the solvent is removed by decompression and evaporation. Next dissolve the residue in 30 mL n-hexane. The n-hexane is decompressed and condensed. By a separation and purification technique-liquid chromatography (SiO$_2$, ethyl acetate:n-hexane=1:10), the products C7 (0.892 g, 1.9 mmol) and MSnBG (0.266 g, 90.2%) are obtained.

Analysis of the synthesis product: IR (neat) ν 3382 (NH), 1716 (CO) cm$^{-1}$. $^1$H NMR (CDCl$_3$) δ 9.60-9.30 (br, 2 H, NH$_2$), 7.20-7.13 (m, 4 H, C$_6$H$_4$), 5.17 (s, 2 H, CH$_2$C$_6$H$_4$), 1.60-1.48 (m, 6 H, CH$_2$CH$_3$), 1.49 (s, 9 H, C(CH$_3$)$_3$), 1.30 (s, 9 H, C(CH$_3$)$_3$), 1.38-1.27 (m, 6 H, CH$_2$CH$_2$CH$_3$), 1.03 (m, 6 H, CH$_2$Sn), 0.88 (t, J=7.2 Hz, 9 H, CH$_2$CH$_3$). $^{13}$C NMR (CDCl$_3$) δ 163.75 and 161.0 (CO), 155.02 (C=N), 141.59, 138.22, 134.87, 134.76, 127.61 and 126.40 (C$_6$H$_4$), 83.76 and 78.72 (C(CH$_3$)$_3$), 47.70 (CH$_2$C$_6$H$_4$), 29.03 (CH$_2$CH$_3$), 28.27 and 27.71 (C(CH$_3$)$_3$), 27.30 (CH$_2$CH$_2$Sn), 13.62 (CH$_3$CH$_2$), 9.46 (CH$_2$Sn). MS m/z cluster peaks at 639 (M$^+$), 582 (M$^+$–C(CH$_3$)$_3$)○

Figure 4:
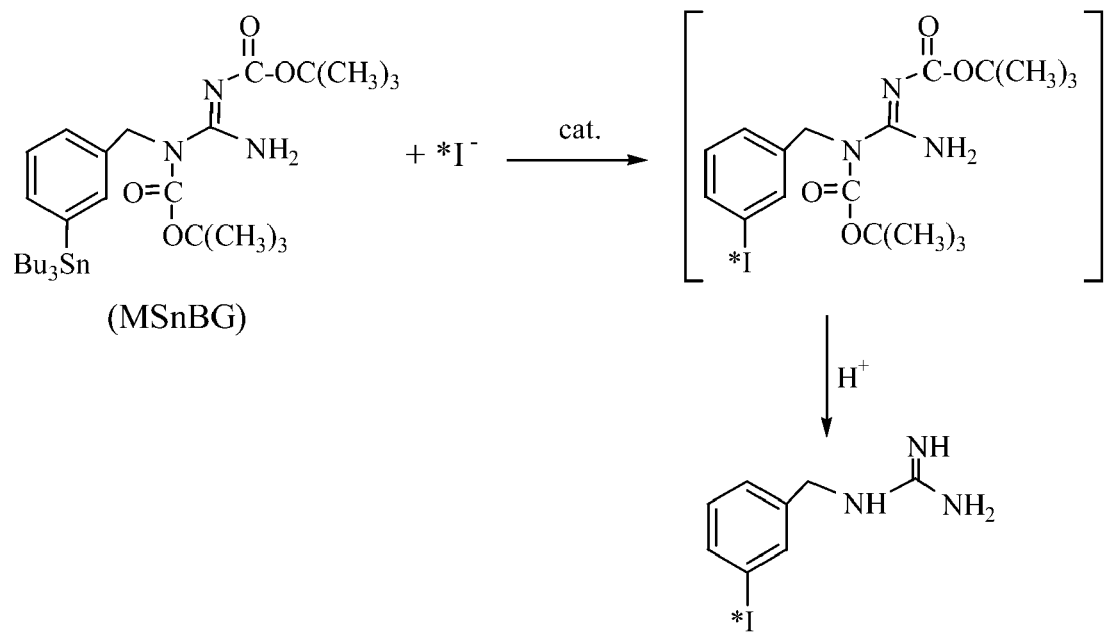
FIG. 4 are reaction equations showing preparation of [*I] MIBG by a precursor MSnBG according to the present invention.

The present invention is based on the following idea: the natural iodine in the compound is replaced by a leaving group Bu$_3$Sn that is easily released to form a precursor. Then a substitution is used to prepare radiopharmaceuticals. The Bu$_3$Sn group is replaced by [*I]$^+$ ion so that the products contain no natural iodine, as shown in FIG. 4.

In summary, the present invention has following advantages:

1. According to the present invention, 3-iodobenzylguanidine bicarbonate is obtained by an addition reaction between 3-iodobenzylamine hydrochloride (C1) and cyanamide (C2) under heating without solvent. After completion of the reaction, the product is dissolved in water and is added with aqueous solution of sodium bicarbonate so as to generate insoluble 3-iodobenzylguanidine bicarbonate (C4) precipitate. After filtering and washing, a compound C4 with high purity is obtained. There are no complicated separation and purification processes.

2. In the present invention, the protection reaction of NH group of the compound C4 is in dimethyl sulfoxide (DMSO)(C5) solvent. The advantage of this solvent is in that both the compound C4 and the protecting agent-di-tert-butyl dicarbonate (C6) are dissolved in the solvent C5 while the product-N,N'-bis(tert-butyloxycarbonyl)-N-(3-iodobenzyl) guanidine (C7) is insoluble in the solvent C5 and is precipitated. After completion of the reaction, filtering and washing, the compound C7 is obtained. There are no complicated separation and purification processes.

3. In the substitution reaction between the compound C7 and bis(tri-n-butyltin) (C8), the solvent is 1,4-dioxane (C10) and bis(triphenylphosphine) palladium dichloride (C9) is a catalyst. React at 80 degrees Celsius, the yield rate of MSnBG is over 90%.

4. In the present invention, the Bu$_3$Sn of the precursor MSnBG is an optimal leaving group that is easily replaced in a substitution reaction.

5. The protecting group for NH group of MSnBG is Boc ((CH$_3$)$_3$OCO) that is stable in alkaline solution but is easy to be hydrolyzed and released in acid solution. Thus after the completion of the substitution reaction between MSnBG and radioactive iodine, a certain amount of acid is added so as to remove the protecting group Boc and obtain the radioactive drug-[*I]MIBG. The preparation processes are relatively simple.

6. The MSnBG is used in no-carrier-added synthesis of [*I] MIBG. The [*I]MIBG obtained by this method has better effect on neuroblastoma treatment than that obtained by conventional, carrier-added method.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method for preparing a precursor of radioactive 3-iodobenzylguanidine comprising the steps of:
melting mixture of 3-iodobenzylamine hydrochloride and cyanamide, and then dissolving it in water, adding sodium bicarbonate so as to make 3-iodobenzylguanidine bicarbonate precipitate;
using di-tert-butyl dicarbonate as a protecting agent for NH group and converting 3-iodobenzylguanidine bicarbonate into N,N'-bis(tert-butyloxycarbonyl)-N-(3-iodobenzyl) guanidine in dimethyl sulfoxide solution; and
using palladium compounds as a catalyst of a substitution reaction between N,N'-bis(tert-butyloxycarbonyl)-N-(3-iodobenzyl)guanidine and bis(tri-n-butyltin) occurring in 1,4-dioxane and obtaining N,N'-bis(tert-butyloxycarbonyl)-3-(tri-n-butyltin)benzylguanidine (MSnBG) by the substitution reaction between N,N'-bis(tert-butyloxycarbonyl)-N-(3-iodobenzyl)guanidine and bis(tri-n-butyltin) occurring in 1,4-dioxane.

2. The method as claimed is claim 1, wherein in the step of melting mixture of 3-iodobenzylamine hydrochloride and cyanamide, melting temperature ranges from 80 degrees Celsius to 120 degrees Celsius.

3. The method as claimed is claim 1, wherein in the step of using di-tert-butyl dicarbonate as a protecting agent for NH group, a solvent for the protecting agent is dimethyl sulfoxide or N,N-dimthylformamide.

4. The method as claimed is claim 1, wherein in the step of using di-tert-butyl dicarbonate as a protecting agent for NH group, reaction temperature ranges from 20 to 70 degrees Celsius.

5. The method as claimed is claim 1, wherein in the step of using palladium compounds as a catalyst of a substitution reaction between N,N'-bis(tert-butyloxycarbonyl)-N-(3-iodobenzyl)guanidine and bis(tri-n-butyltin) occurring in 1,4-dioxane and obtaining N,N'-bis(tert-butyloxycarbonyl)-3-(tri-n-butyltin trinbutyltin)benzylguanidine (MSnBG) by a substitution reaction between N,N'-bis(tert-butyloxycarbonyl)-N-(3-iodobenzyl)guanidine and bis(tri-n-butyltin) occurring in 1,4-dioxane, a solvent for the substitution reaction is 1,4-dioxane, triethylamine, or tetrahydrofaran.

6. The method as claimed is claim 1, wherein in the step of using palladium compounds as a catalyst of a substitution reaction between N,N'-bis(tert-butyloxycarbonyl)-N-(3-iodobenzyl)guanidine and bis(tri-n-butyltin) occurring in 1,4-dioxane and obtaining N,N'-bis(tert-butyloxycarbonyl)-3-(tri-n-butyltin)benzylguanidine (MSnBG) by a substitution reaction between N,N'-bis(tert-butyloxycarbonyl)-N-(3-iodobenzyl)guanidine and bis(tri-n-butyltin) occurring in 1,4-dioxane, the catalyst for the substitution reaction is bis(triphenylphosphine)palladium(II) dichlonide or tetrakis(triphenylphosphine)palladium(0).

7. The method as claimed is claim 1, wherein in the step of using palladium compounds as a catalyst of a substitution reaction between N,N'-bis(tert- butyloxycarbonyl)-N-(3-iodobenzyl)guanidine and bis(tri-n-butyltin) occurring in 1,4-dioxane and obtaining N,N'-bis(tert-butyloxycarbonyl)-3-(tri-n-butyltin)benzylguanidine (MSnBG) by a substitution reaction between N,N'-bis(tert-butyloxycarbonyl)-N-(3-iodobenzyl)guanidine and bis(tri-n-butyltin) occurring in 1,4-dioxane, temperature of the substitution reaction ranges from 60 degrees Celsius to 100 degrees Celsius.

* * * * *